(12) United States Patent
Bearinger

(10) Patent No.: US 11,320,432 B2
(45) Date of Patent: *May 3, 2022

(54) SYSTEM WITH BUFFER FOR LATERAL FLOW ON A POROUS MEMBRANE

(71) Applicant: LAWRENCE LIVERMORE NATIONAL SECURITY, LLC, Livermore, CA (US)

(72) Inventor: Jane P. Bearinger, Berwyn, PA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 82 days.

This patent is subject to a terminal disclaimer.

(21) Appl. No.: 15/677,992

(22) Filed: Aug. 15, 2017

(65) Prior Publication Data

US 2018/0024130 A1    Jan. 25, 2018

Related U.S. Application Data

(62) Division of application No. 13/893,315, filed on May 13, 2013, now Pat. No. 9,804,161.

(60) Provisional application No. 61/646,436, filed on May 14, 2012.

(51) Int. Cl.
| | | |
|---|---|---|
| *G01N 33/558* | (2006.01) | |
| *G01N 33/53* | (2006.01) | |
| *G01N 33/543* | (2006.01) | |

(52) U.S. Cl.
CPC .......... *G01N 33/558* (2013.01); *G01N 33/53* (2013.01); *G01N 33/54306* (2013.01); *G01N 33/54366* (2013.01); *C07K 2317/32* (2013.01); *G01N 2470/06* (2021.08); *Y10S 435/97* (2013.01); *Y10S 435/973* (2013.01)

(58) Field of Classification Search
CPC ............ G01N 33/558; G01N 33/54386; Y10S 435/97
USPC ....................................................... 436/514
See application file for complete search history.

(56) References Cited

U.S. PATENT DOCUMENTS

| | | | | |
|---|---|---|---|---|
| 5,415,994 A * | 5/1995 | Imrich | .................. | B01L 3/5023 435/5 |
| 5,451,504 A * | 9/1995 | Fitzpatrick | ........... | G01N 33/558 435/7.2 |
| 5,580,794 A * | 12/1996 | Allen | .................... | B01L 3/5023 422/404 |
| 5,731,162 A | 3/1998 | Gatti et al. | | |
| 6,100,099 A * | 8/2000 | Gordon | .............. | C07K 14/4712 422/561 |
| 6,686,170 B1 | 2/2004 | Flanders et al. | | |
| 6,753,190 B1 * | 6/2004 | Okada | .................. | G01N 33/543 435/4 |
| 7,700,372 B2 | 4/2010 | Nylese | | |
| 7,749,712 B2 * | 7/2010 | Pulli | ...................... | C07K 16/44 435/7.1 |
| 8,956,859 B1 * | 2/2015 | Bermudes | ............ | G01N 33/558 435/287.7 |
| 9,804,161 B1 | 10/2017 | Bearinger | | |
| 2003/0157729 A1 | 8/2003 | Thayer et al. | | |
| 2005/0186111 A1 | 8/2005 | Wang et al. | | |
| 2007/0042499 A1 | 2/2007 | Schwind et al. | | |
| 2007/0134811 A1 | 6/2007 | Takeuchi et al. | | |
| 2008/0138842 A1 * | 6/2008 | Boehringer | ...... | G01N 33/54306 435/7.94 |
| 2010/0112726 A1 * | 5/2010 | Badwan | ........... | G01N 33/54306 436/530 |
| 2012/0071342 A1 | 3/2012 | Lochhead et al. | | |
| 2012/0184462 A1 | 7/2012 | O'Farrell et al. | | |
| 2015/0197579 A1 * | 7/2015 | Stefan | .................. | C07K 16/243 506/9 |
| 2017/0370930 A1 | 12/2017 | Bearinger | | |
| 2018/0224378 A1 | 8/2018 | Kay et al. | | |

FOREIGN PATENT DOCUMENTS

| | | | | |
|---|---|---|---|---|
| DE | 10000322 C2 | 10/2003 | | |
| WO | WO-9731268 A1 * | 8/1997 | ........... | G01N 33/558 |
| WO | WO-2005098439 A2 * | 10/2005 | ............... | B82Y 5/00 |

OTHER PUBLICATIONS

Rizk et al. "Allosteric control of ligand-binding affinity using engineered conformation-specific effector proteins", Nature Structural & Molecular Biology vol. 18, pp. 437-442 (2011), doi:10.1038/nsmb.2002 (Year: 2011).*
Harlow, E. and Lane, D., Antibodies: A Laboratory Manual (1988) Cold Spring Harbor Laboratory Press, Cold Spring Harbor, NY, pp. 23-26 (Year: 1988).*
Harlow E. et al., "Antibodies: A Laboratory Manual" *Cold Spring Harbor Laboratory*, 1988; pp. 553, 578-581; 7 pages.
Non-Final Office Action for U.S. Appl. No. 15/677,961, filed Aug. 15, 2017 on behalf of Lawrence Livermore National Security LLC. dated Oct. 11, 2019 21 pages.
Restriction Reguirement for U.S. Appl. No. 15/677,961, filed Aug. 15, 2017 on behalf of Lawrence Livermore National Security, LLC. dated Jun. 17, 2019. 5 pages.
Final Office Action for U.S. Appl. No. 15/677,961, filed Aug. 15, 2017 on behalf of Lawrence Livermore National Security, LLC. dated Jul. 6, 2020. 21 pages.
Non-Final Office Action for U.S. Appl. No. 15/677,961, filed Aug. 15, 2017 on behalf of Lawrence Livermore National Security, LLC dated Jun. 8, 2021 24 pages.

* cited by examiner

*Primary Examiner* — Ellen J Marcsisin
(74) *Attorney, Agent, or Firm* — Steinfl + Bruno LLP

(57) ABSTRACT

Systems are described, based on a primary binding compound and a secondary binding compound used in combination with a support to detect a target in a sample. The systems includes at least one support structure, at least one small primary support portion containing at least one molecule covalently bound to a visual colloidal marker, a plurality of secondary support portions comprising secondary binding compounds that are covalently bound to the support portions and chemically active, at least one pH litmus indicator, at least one pH strip, a buffer for lateral flow on the porous membrane support that allows preservation and activity of binding compounds.

11 Claims, 7 Drawing Sheets

SYSTEM WITH BUFFER FOR LATERAL FLOW ON A POROUS MEMBRANE

CROSS REFERENCE TO RELATED APPLICATIONS

The present application is the divisional application of U.S. patent application Ser. No. 13/893,315 filed on May 13, 2013 now U.S. Pat. No. 9,804,161 issued on Oct. 31, 2017, which claims priority to U.S. Provisional Application No. 61/646,436 entitled "Disposable STD panel Detector" filed on May 14, 2012, all of which are incorporated herein by reference in their entirety.

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD

The present disclosure relates to a detector and related devices, methods and systems. In particular, the present disclosure and related devices, methods and device for detection of a target.

BACKGROUND

High sensitivity detection of targets and in particular of biomarkers has been a challenge in the field of biological molecule analysis, in particular when aimed at detection of a plurality of targets and/or at detection of a target of a certain dimension or present in the sample at a low concentration.

Whether for pathological examination or for fundamental biology studies, several methods are commonly used for the detection of various classes of biomaterials and biomolecules.

There are numerous health, quality, security control, and other applications that require effective detection of targets by detectors. However, development of target detectors has been challenging especially in connection with achievement of a specific and sensitive detection.

SUMMARY

Provided herein is a detector and related devices, methods and systems that, in several embodiments allow interaction between binding compounds and molecules, for the purpose of detection. In particular, in some embodiments devices methods and systems herein described facilitate the specific interaction of suitable binding compounds and molecules wherein detection is performed for the purpose of diagnosing.

According to a first aspect a support is described. The support comprises a first support portion and at least one second support portion distinct from the first support portion. In the support, the first support portion is configured to bind to at least one target and host a respective at least one first binding compound specific to the at least one target. In the support, the at least one second support portion hosts a respective at least one second binding compound specific to the at least one target. In the support, the at least one first binding compound comprising a corresponding at least one label, and the at least one second binding compound is different from and non-competitive with respect to the at least one first binding compound for a same target.

According to a second aspect, a detection system is described. The detection system comprises: a liquid medium and a solid medium. In the detection device, the liquid medium hosts a first binding compound specific to a target, the first binding compound comprising a label. In the detection device, the solid medium hosts a second binding compound specific to the target, the second binding compound being different from and non-competitive with respect to the first binding compound.

According to a third aspect a method and a system for detecting molecules from a support is described. The method comprises: combining a sample with a medium that allows binding reactions to occur and applying a labeled complex to one side of a support that allows fluid to be drawn through. The method further comprises bringing the labeled complex across the support by lateral flow, combining the complex with a second binding compound specific to the target, and deriving information pertaining to the target molecule via a visual signal. The systems comprises at least two of a support, a medium that allows binding reactions to occur, a labeled complex and a second binding compound specific to the target, for simultaneous combined or sequential use in the method herein described.

According to the fourth aspect a method and system for detecting molecules from a detection device is described. The method comprising: combining a sample with a first binding compound specific to a target to form a complex, the first binding compound comprising a label, applying the labeled complex to one side of a support, and bringing the labeled complex across the support by lateral flow. The method further comprises combining the complex with a second binding compound specific to the target, and deriving information pertaining to the target molecule via a visual signal. The system comprises at least two of a first binding compound specific to a target and comprising a label, a support, and a second binding compound specific to the target for simultaneous combined or sequential use in the methods herein described.

According to a fifth aspect a method and system of manufacturing a detection device are described. The method comprises: treating of a support for the lateral flow of fluids, applying a primary reservoir on the support to maintain a chemical in a form for binding, creating a solution for applying the primary binding compound to the primary reservoir of the support; and applying the primary binding component to maintain a binding capability in a preserved format. The method further comprises applying a secondary reservoir on a support for a secondary binding compound; creating a solution for applying the secondary compound to maintain the integrity of the secondary compound on the support, applying a secondary binding compound onto the support in a solution to maintain the binding capabilities, and applying a control reservoir with reagents to bind to a carrier medium in a preserved format. The method also comprises creating a reservoir for a pH litmus indicator for a solution carrying biomolecules, and creating a reservoir for a pH test for a solution carrying biomolecules. The system comprises, at least two of: a support, a primary reservoir, a secondary reservoir, a primary binding component, a secondary binding component and a reservoir for a pH litmus indicator for simultaneous combined or sequential use in the methods herein described.

According to a sixth aspect, a method and a system of manufacturing a support are described. The method comprises: treating of a support to allow the lateral flow of fluids, creating a solution for mixing the primary binding compound to the solution sample to allow binding of compounds, applying a reservoir on the support to maintain the chemical or molecule in a form for binding, applying the binding component to maintain a binding capability in a preserved format, applying a secondary reservoir on a support for a secondary binding compound, creating a solution for applying the secondary compound to maintain the integrity of the secondary compound on the support, applying a secondary binding compound onto the support in a solution to maintain the binding capabilities, applying a control reservoir with reagents to bind to a carrier medium in a preserved format, creating a reservoir for a pH litmus indicator for a solution carrying biomolecules, and creating a reservoir for a pH test for a solution carrying biomolecules.

According to a seventh aspect, a system is described. The system comprises a support possibly composed of nylon or cellulose, a small primary support portion containing at least one molecule covalently bound to a visual colloidal marker, a plurality of secondary support portions comprising secondary binding compounds that are covalently bound to the support portions and chemically active, a pH litmus indicator, a pH strip, and a buffer for lateral flow on the porous membrane support that allows preservation and activity of binding compounds.

The support, devices, methods and systems herein described, and related compositions, can be used in connection with applications wherein detection of a target is desired. Exemplary applications comprise detection of targets in medical and/or biological applications, possibly directed to detection of biomarker or biomolecules such as antigen for one or more conditions, such as RNA and/or DNA molecule or protein from single or mixed DNA and RNA viruses derived from clinical samples and additional applications which are identifiable by a skilled person.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

Figure 1:
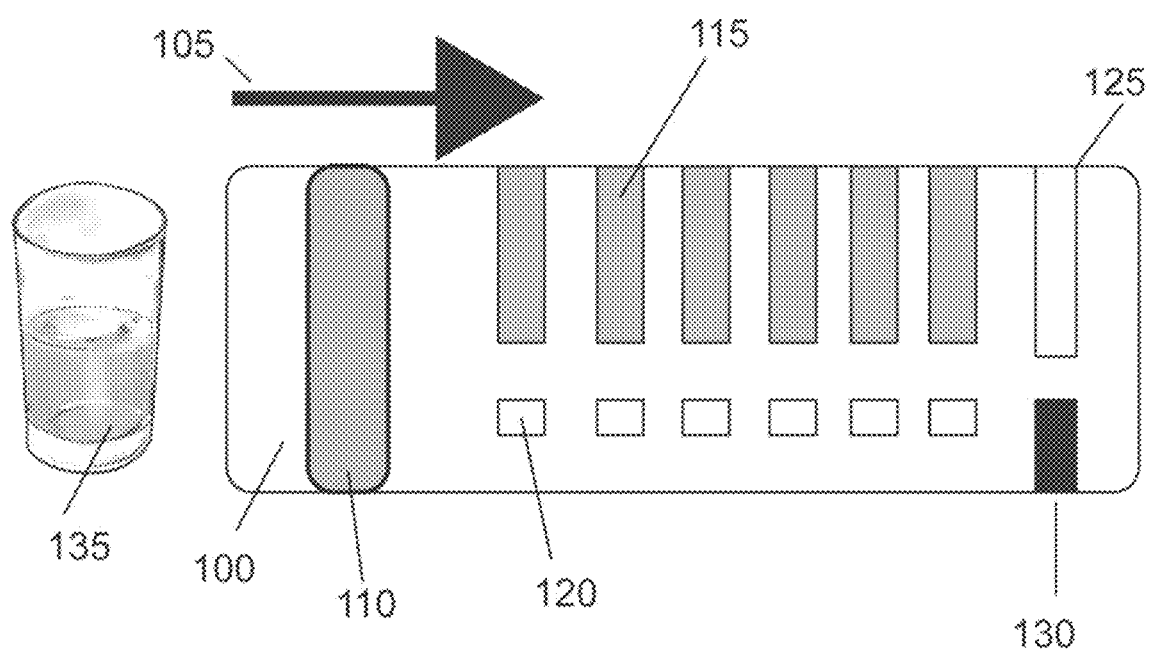
FIG. 1 shows a schematic illustration of a lateral flow based disposable device with a first reservoir for binding compounds, followed by lanes of reservoirs for second binding compounds, a pH control strip, and a pH indicator.

Described herein are various embodiments directed at the detection of a target in sample.

The terms "detect" or "detection" as used herein indicates the determination of the existence, presence or fact of a specific target in a limited portion of space, including but not limited to a sample, a reaction mixture, or other limited portion of space identifiable to a skilled person upon a reading of the present disclosure. The detection can be quantitative or qualitative. A detection is "quantitative" when it refers to, relates to, or involves the measurement of quantity or amount of the target or signal (also referred as quantitation), which includes but is not limited to any analysis designed to determine the amounts or proportions of the target or signal. Detection is "qualitative" when it refers to, relates to, or involves identification of a quality or kind of the target or signal in terms of relative abundance to another target or signal, which is not quantified.

The term "target" as used herein indicates an analyte of interest. The term "analyte" refers to a substance, compound, moiety, or component whose presence or absence in a sample is to be detected. Analytes include but are not limited to biomolecules and in particular biomarkers. The term "biomolecule" as used herein indicates a substance, compound or component associated with a biological environment including but not limited to sugars, amino acids, peptides, proteins, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state. The "biological environment" refers to any biological setting, including, for example, ecosystems, orders, families, genera, species, subspecies, organisms, tissues, cells, viruses, organelles, cellular substructures, prions, and samples of biological origin.

The term "sample" as used herein indicates a limited quantity of something that is indicative of a larger quantity of that something, including but not limited to fluids from a biological environment, a bodily fluid, a specimen, cultures, tissues, commercial recombinant proteins, synthetic compounds or portions thereof. The term "bodily fluid" can include blood, lymphatic fluid, cerebrospinal fluid, urine, saliva, vaginal fluid, digestive fluids and additional fluids identifiable by a skilled person.

In some embodiments, target detection according to the present disclosure can be performed with a support comprising a first support portion and at least one second support portion distinct from the first support portion. The first support portion can be configured to bind to at least one target and host a respective at least one first binding compound specific to the at least one target. The at least one second support portion can host a respective at least one second binding compound specific to the at least one target.

Attention is drawn to FIG. 1, which depicts a schematic top view of one embodiment of the present disclosure, wherein a first reservoir or support portion (110) is on one side of a support (100) containing a first binding compound that is specific to a target and comprises a visual label. This is followed by a number of periodically spaced secondary reservoirs that contain reagents to capture a complex composed of the target and first binding compound (115) and is fabricated on the support (100).

The term "support" as used herein indicates an inert material, usually solid, that is configured to attach one or more compounds of interest and to allow flow of a fluid through the material (e.g. by capillary flow or lateral flow). An exemplary structure configured to be used as a support comprises voids allowing fluid communication between different portions of the structure. The voids can attach one or more compounds presented on the voids to bind at least one target possibly present in the fluid. Supports can be of various thicknesses, with homogeneous or heterogeneous structure. Supports can be comprised within, for example, flat sheets, or bundles of full or hollow fibers. Exemplary supports in the sense herein described comprise magnetic materials, such as beads configured to attach binding compounds, polymer gel structure, siliconized microtiter plates, textile materials, or other platforms identifiable by a skilled person.

The term "binding compound" or "capture agent" as used herein indicates a molecule that can specifically bind to a target, e.g. through the specific binding of one or more of molecule binding sites. Binding compounds herein described can include molecules of various chemical natures such as polypeptides (e.g. antibodies or receptors), polynucleotides (e.g. DNA or RNA) and/or small molecules (e.g. aptamers), as well as other molecules capable of specific binding identifiable by a skilled person upon reading of the present disclosure.

In embodiments herein described, one or more binding compounds can be attached to one or more materials forming the support typically through functional groups capable of interacting with corresponding functional groups presented on the one or more materials.

The term "functional group" as used herein indicates specific groups of atoms within a molecular structure that are responsible for the characteristic chemical reactions of that structure. Exemplary functional groups include hydrocarbons, groups containing halogen, groups containing oxygen, groups containing nitrogen and groups containing phosphorus and sulfur all identifiable by a skilled person. In particular, functional groups in the sense of the present disclosure include a carboxylic acid, amine, triarylphosphine, azide, acetylene, sulfonyl azide, thio acid and aldehyde. In particular, for example, the first functional group and the second functional group can be selected to comprise the following binding partners: carboxylic acid group and amine group, azide and acetylene groups, azide and triarylphosphine group, sulfonyl azide and thio acid, and aldehyde and primary amine. Additional functional groups can be identified by a skilled person upon reading of the present disclosure. As used herein, the term "corresponding functional group" refers to a functional group that can react with another functional group. Thus, functional groups that can react with each other can be referred to as corresponding functional groups. In embodiments where the corresponding functional groups are in the support and in the binding component the corresponding functional group react to form a covalent bond, a hydrogen bond or other bond functional to the attachment of the polymer component and the binding component identifiable by a skilled person upon reading of the present disclosure.

The term "attach" or "attachment" as used herein, refers to connecting or uniting by a bond, link, force or tie in order to keep two or more components together, which encompasses either direct or indirect attachment such that, for example, a first compound is directly bound to a second compound or material, and the embodiments wherein one or more intermediate compounds, and in particular molecules, are disposed between the first compound and the second compound or material. In particular, in some embodiments, the binding compounds can be associated with the support by, for example, by being physically embedded in the support material, by being covalently bonded to the support material, or through a combination of both.

Attachment of the binding compound to the support can be verified for example by targeting the support with antibody specific for the binding compound of interest, detection on the support of chemical and/or biological properties of the binding compound and additional techniques identifiable by a skilled person In embodiments of the support herein described, the at least one first binding compound comprises a corresponding at least one label, and the at least one second binding compound is different from and non-competitive with respect to the at least one first binding compound for a same target.

The terms "label" and "labeled molecule" as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof, which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

The wording "non-competitive binding" as used herein refers to the binding of a binding compound to a target that does not interfere with the binding of second binding compound to the same target. By way of example but not of limitation, a binding compound such as an antibody is considered to non-competitively bind to a target, if both the first and second antibody to the target have different binding sites or different epitopes on the same target, and can bind to the target simultaneously to form a stable complex. The confirmation of a complex comprising three different compounds can be confirmed by analytical size exclusion gel filtration, where one would expect that a compound alone would result in a single peak at a specific elution time during elution that also correlates to the molecular weight of the single compound. Upon adding the second and third compound, one would expect a different elution time that correlates to a larger size indicative of a complex. Size exclusion gel filtration is a common technique for determining size and protein binding and should be known to a person skilled in the art. In several embodiments of the present disclosure, a lateral flow device is described that has a target that is first bound by antibodies raised against the target. A second set of antibodies to the same target can then bind, although it can bind to a different epitope on the target.

In particular, binding between compounds in detectors, methods and systems herein described and more particularly non-competitive binding between binding compounds and the target can be a specific binding.

The wording "specific", "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Binding compounds able specifically bind one to the other to form a stable complex display an affinity to bind to the corresponding target. This affinity can take any form. For example, such affinity can be described in terms of non-covalent interactions, such as the type of binding that occurs in enzymes that are specific for certain substrates and is detectable. Typically those interactions include several weak interactions, such as hydrophobic, van der Waals, and hydrogen bonding which typically take place simultaneously. Exemplary specific bindings are antibody-antigen interaction, cellular receptor-ligand interactions, polynucleotide hybridization, enzyme substrate interactions and additional binding identifiable by a skilled person. The term "specific" as used herein with reference to a molecular component of a complex, refers to the unique association of that component to the specific complex which the component is part of. By "stable complex" is meant a complex that is detectable and does not require any arbitrary level of stability, although greater stability is generally preferred.

Reference is made to the exemplary illustration of FIG. 1 and in particular to the schematic illustration of the first reservoir or support portion (110) containing a first binding compound or primary binding compound specific to a target and second reservoirs (115) containing a second binding compound or secondary binding compound capable of specific binding to the target, the binding of the secondary compound with the target non-competitive with the binding of the primary binding compound. The first binding compound in the support portion (110) can also contain a label and in particular a visual marker for detection and can concentrate on the secondary reservoirs or supports (115) with the second binding compound. In some embodiments, the secondary reservoirs (115) are periodically spaced with respect to one another and can have positive control strips (120) possibly located alongside reservoirs (115) on the support (100). The medium, a bulk solution, gel or fluid (135), can contain the target of interest, and can flow through the support, e.g. by lateral flow, in one direction (105). The medium containing the target can flow past the first reservoir or support (110) to bind the target with the first binding compound, forming a target compound complex. The target-compound complex can flow towards the second reservoir or support (115) where the target complex is captured by the second binding compound and the local concentration of the target-compound complex is increased and can be visualized through detection of the label bound to the first compound, giving e.g. a colorimetric signal. The control regions (120) can react with reagents in the medium as the medium flows through the substrate (100). According to an exemplary embodiment of the present disclosure the control regions (120) are of rectangular shape. The control regions (120) as well as any other region or portions on the support can be of any other shape including shapes such as alphabetical letters (see e.g. the exemplary schematic illustration of FIG. 6 and FIG. 7). In the illustration of FIG. 1 the second reservoir can be followed by a pH control region in the form of a control strip (130) and a pH indicator (125). In particular, in some embodiments, the control strip (130) can have bound antibodies or other capture agents that bind directly to secondary antibodies attached to nanoparticles or the like (e.g. colloidal particles) which may be present in the buffer.

In some embodiments, the control region such as control strip (120) in the exemplary illustration of FIG. 1, can contain a binding compound that can bind to the unbound primary binding compound and can elicit a signal. In some embodiments, the control region of the support can contain a binding compound to the bulk solution as a positive control or a binding compound that can specifically target the unbound primary binding compound as a control. For example in some of those embodiments, the control strip (120) can contain an antibody that can specifically target the unbound primary compound as a positive control to show that the assay is working.

Figure 2:
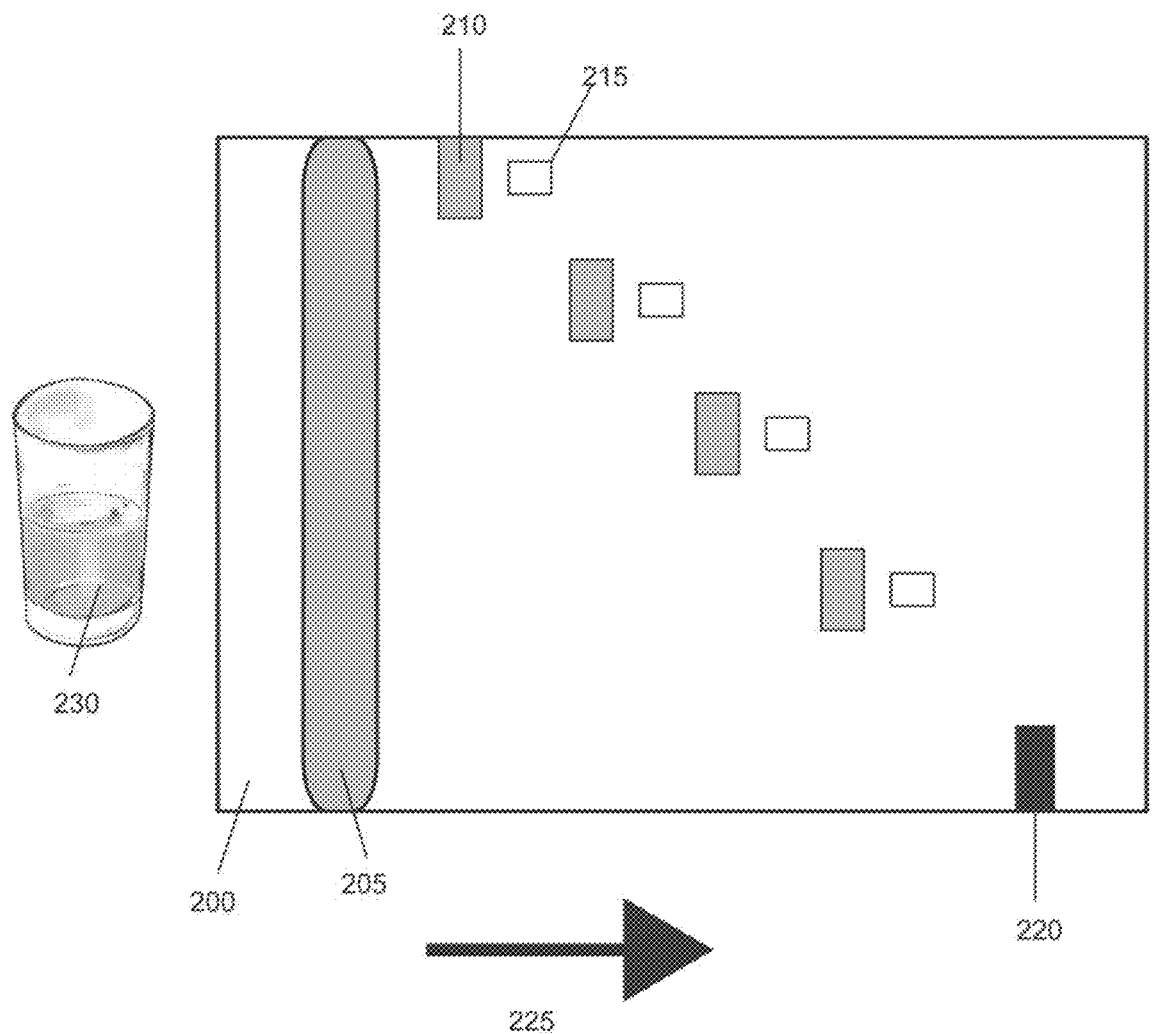
FIG. 2 depicts an additional embodiment of a lateral flow based disposable device of FIG. 1, with a first reservoir for binding compounds, followed by a second reservoir depicted as lanes that contain the second binding compounds that are staggered throughout the device to prevent cross reactivity, and a pH control strip.

Reference is also made to FIG. 2, which depicts a schematic top view of another exemplary embodiment of the present disclosure. Similarly to the previous depiction of FIG. 1, FIG. 2 has a first reservoir or support portion (205) on one side of the support (200) and contains a first binding compound comprising a label that is specific to a target. In the illustration of FIG. 2, a second reservoir or support portion (210) comprised of a plurality of spaced regions that contains a secondary compound to capture the target-compound complex (210) are staggered, to minimize cross reactivity of other targets and complexes in the medium, as exemplified in the figure (FIG. 2). Control strips for the reagent (215) are also staggered and the medium flows in one direction (225). Similar to the previous exemplary embodiment of FIG. 1, medium containing the target flow past the first reservoir (205) and the target forms a complex with the first binding compound. In the exemplary illustration of FIG. 2, the target-compound complex then flows towards the second reservoir (210), where it is captured and leads to detectable signal such as a colorimetric signal. In some embodiments, the second reservoir (210) and control strip (215) can be followed by a pH control strip (220) on the substrate (200).

Figure 3:
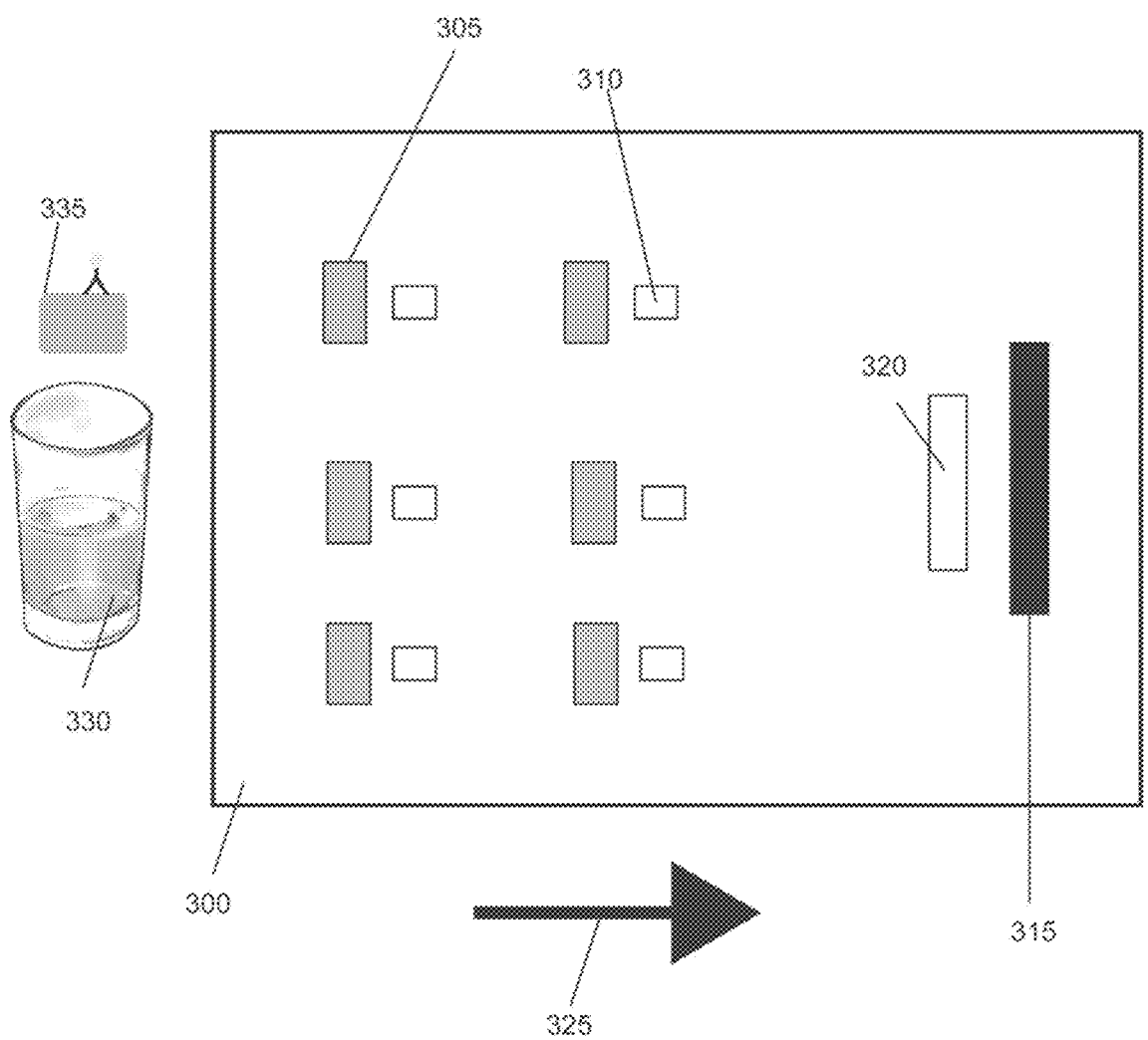
FIG. 3 depicts a schematic of an immersed disposable lateral flow based device with a series of reservoir depicted as lanes for binding reagents, a pH indicator, and a pH control strip.

Reference is also made to FIG. 3, which depicts a schematic top view of another embodiment of the present disclosure. Similar to the previous schematics of FIG. 1 and FIG. 2, FIG. 3 shows an exemplary schematics of further embodiment of the present disclosure, in the form of an immersed detection device, where a support (300) contains several reservoirs or support portions (305) containing reagents to capture only a target-compound complex. A pH control strip (315) and a pH indicator (320) are present on the substrate (300). In one embodiment, target molecules are placed in a medium, a liquid, containing a first binding compound that can specifically bind target molecules contained in the medium. By way of example and not of limitation, the medium containing the target-compound complex can be placed onto the support and is transported in one direction (325) on the device by lateral flow towards the reservoir containing reagents to capture the target-compound complex (305) and towards adjacent control strips (310). When the target complex reaches the reservoir or support portion that binds specifically to the target or complex, the target concentration can be locally enhanced at that region (305) and a signal can be visualized. The medium can then flow towards the pH indicator (320) and the pH control strip (315).

For example in some embodiments of the detector, methods and systems herein described wherein the support of FIG. 3 is used, a sample is placed in a medium, e.g. a liquid (330), containing a first binding compound that can specifically bind target molecules contained in the medium and then be placed on the support (300) and allowed to flow towards a plurality of support portions (305) containing reagents to capture an already formed target-compound complex (335), towards control region (310), pH control strip (315) and pH indicator (320). In the present disclosure the first binding compound is an IgG antibody containing a visual marker such as colloidal gold, magnetic particles, or quantum dots. In particular, in some embodiments, when the target-compound complex reaches the support portion that binds specifically to the target or complex, the target concentration is locally enhanced at that region (305) and a signal can be detected. In embodiments wherein the label is a visual marker the captured complex can then be visualized as concentration of complex is concentrated on the support. The visual marker that is seen can be the concentrated colloidal material such as colloidal gold, colloidal quantum dots, or colloidal magnetic particles. The signal can be a color such as a color red if bound to the colloidal gold label. The medium can then flow towards the pH indicator (320) and the pH control strip (315).

In embodiments of detectors, methods and systems herein described, the sample can be an environment sample collected from water, soil, air or outer space, samples collected from a surface of a facility, equipment or system, food or pharmaceutical preparation, as well as drinking water, agricultural irrigation water and other samples identifiable to a skilled person upon a reading of the present disclosure. In some embodiments, the samples can comprise bodily fluids such as blood, urine, vaginal fluids, expectorates and additional bodily fluids identifiable by a skilled person.

In some embodiments the target and/or the binding compound can be a protein or a polynucleotide. The term "protein" as used herein indicates a polypeptide with a particular secondary and tertiary structure that can interact with and in particular bind another analyte and in particular, with other biomolecules including other proteins, DNA, RNA, lipids, metabolites, hormones, chemokines, and small molecules. The term "polypeptide" as used herein indicates an amino acid polymer of any length including full length proteins and peptides, as well as analogs and fragments thereof. A polypeptide of three or more amino acids is also called a protein oligomer, peptide or oligopeptide. In particular, the terms "peptide" and "oligopeptide" usually indicate a polypeptide with less than 50 amino acid monomers. As used herein the term "amino acid", "amino acidic monomer", or "amino acid residue" refers to any of the twenty naturally occurring amino acids, non-natural amino acids, and artificial amino acids and includes both D an L optical isomers.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or with a different functional group. Accordingly, the term "polynucleotide" includes nucleic acids of any length, and in particular DNA, RNA, analogs and fragments thereof. A polynucleotide of three or more nucleotides is also called "nucleotidic oligomer" or "oligonucleotide."

In embodiments, herein described polynucleotides and/or peptides can be comprised in detectors, methods and systems herein described in form of aptamers. The term "aptamers" as used here indicates oligonucleic acid or peptide molecules capable of specific binding. In particular, nucleic acid aptamers can comprise, for example, nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the antibodies Peptide aptamers are peptides that are designed to specifically bind to and interfere with protein-protein interactions inside cells. In particular, peptide aptamers can be derived, for example, according to a selection strategy that is derived from the yeast two-hybrid (Y2H) system. In particular, according to this strategy, a variable peptide aptamer loop attached to a transcription factor binding domain is screened against the target protein attached to a transcription factor activating domain. In vivo binding of the peptide aptamer to its target via this selection strategy is detected as expression of a downstream yeast marker gene.

In some embodiments, the target and/or binding compound can be a small molecule. The term "small molecule" as used herein indicates an organic compound that is of synthetic or biological origin and that, although might include monomers and/or primary metabolites, is not a polymer. In particular, small molecules can comprise molecules that are not protein or nucleic acids, which play a biological role that is endogenous (e.g. inhibition or activation of a target) or exogenous (e.g. cell signaling), which are used as a tool in molecular biology, or which are suitable as drugs in medicine. Small molecules can also have no relationship to natural biological molecules. Typically, small molecules have a molar mass lower than 1 $kg \cdot mol^{-1}$. Exemplary small molecules include secondary metabolites (such as actinomicyn-D), certain antiviral drugs (such as amantadine and rimantadine), teratogens and carcinogens (such as phorbol 12-myristate 13-acetate), natural products (such as penicillin, morphine and paclitaxel) and additional molecules identifiable by a skilled person upon reading of the present disclosure In some embodiments, the target and/or the binding compound can be a protein and in particular an antibody. The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof or derivative thereof. The terms "fragment" as used herein with reference to antibody indicates any portion of an antibody that retain an immunogenic activity characteristic of the antibody. The term "derivative" as used herein with reference to an antibody, indicates a molecule that is structurally related to the antibody and is derivable from the antibody by a modification that introduces a feature that is not present in the antibody while retaining functional properties of the antibody. Accordingly, a derivative antibody, or of any fragment thereof, FaB or scFv, usually differs from the original antibody or fragment thereof by modification of the amino acidic sequence that might or might not be associated with an additional function not present in the original antibody or fragment thereof. Methods to provide derivative and to test the ability of the derivative to retain the one or more functional properties are identifiable by a skilled person. Exemplary antibodies include IgA, IgD, IgG1, IgG2, IgG3, IgM and the like. Exemplary fragments include Fab Fv, Fab' F(ab')2 scFV, single chain antibodies and the like. A monoclonal antibody is an antibody that specifically binds to and is thereby defined as complementary to a single particular spatial and polar organization of another biomolecule which is termed an "epitope". In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

In embodiments herein described, an antibody can be monoclonal or polyclonal or an antibody preparation thereof and have a specific binding to a target. In some embodiments, the antibody can be used in detectors, methods and systems herein described as antibody preparation in which the antibody, including fragments and derivative thereof, is comprised in a solution together with a suitable vehicle.

In some embodiments, antibodies can be binding compound and/or targets; in some embodiments, antibody can also be raised against targets such as a ligand, or an antibody and used as binding compound. In some embodiments, the antibody can be an IgG antibody.

In embodiments of the detector, methods and systems herein described the IgG or other binding compound can be conjugated with a label to form a suitable substrate which is provided for use in detection. In particular, in some embodiments the label can be a visual marker (see, e.g., visual marker (510) later shown in FIG. 5 of the present application) and the visual marker can be a fluorescent marker, colloidal material, colloidal gold, colloidal quantum dots, magnetic based particles, and additional visual marker identifiable by a skilled person.

Fluorescent markers used in embodiments herein described can comprise any fluorophore or dye such as cyanine, fluorescein, rhodamine, alexa fluors, dylight fluors, ATTO dyes or BODIPY dies. Fluorescent labeling can be performed by covalently attaching a fluorophore to another molecule, such as a protein or nucleic acid. This is generally accomplished using a reactive derivative of the fluorophore that selectively binds to a functional group contained in the target molecule. The most commonly labeled molecules are antibodies, proteins, amino acids and peptides which are then used as specific probes for detection of a particular target. Fluorescent labels are generally used for detection of a protein or other labeled molecule via a fluorescence microscope, flow cytometer or some other fluorescence reading instrument. These can be useful in localization of a target within a cell, through flow cytometry (FACS) analysis, western blot assays, and other immunoanalytical methods.

The term "colloidal material" as used herein refers to a system of finely divided particles that can be approximately 10 to 10,000 angstroms in size. In particular, the term "colloidal gold" refers to pegylated gold particles that can be conjugated with a binding compound, such as an antibody or other proteins, to allow visual detection. In particular, particles dimension can be in the nanometer range, more particularly, the colloidal particles can be nanoparticles of 5 to 500 nanometers. Labels such as colloidal gold have unique optical, electronic, and molecular-recognition properties can be detected not only visually but also through electron microscropy and other techniques identifiable by a skilled person. Production of colloidal conjugates of targets or binding compound can be performed in some embodiments by immunogold conjugation a technique whereby any protein, including antibodies and antigens, can be coupled to gold colloid to produce an immunogold complex. Although there are a variety of applications for immunogold conjugates, primary applications can be used in rapid-test devices used for the diagnosis and monitoring of disease. Gold particles can be used for example to label antibody for identifying surface antigens in direct assays and can be detected through a bright color. The color for detection can range from light purple, reds, greens, and yellows and is dependent on the nanoparticle size of the colloidal gold.

Colloidal gold particles can be prepared by reducing a solution of a simple gold salt, such as potassium tetrachloraurate: small metal particles are formed that can have a negative charge (the negative charge is believed to arise from dichlorogold (I) ions on their outer surface). Their size can be controlled by additives, such as tannic acid. Proteins, which usually have a positive charge in solution near neutral pH, are attracted to the negatively charged surface and can adhere to it. Immunogold probes can be prepared by adsorbing antibodies to the gold particle surface. Binding compounds attached to colloidal labels can be proteins which bind to a specific target, such as a tumor cell surface protein; and additional proteins that take the attached gold particle with them, and label the antigen.

The term "quantum dot based" visualization marker refers to a quantum dot probe conjugated to an antibody and can be used to track targeted biomolecules in real-time. Quantum dot based detection can be more sensitive for easy detection. Quantum-dot-based photoelectrochemical sensors can be used for the detection of chemicals and biochemical molecules compared to other sensor types, and can be used nanotechnology-related analytical methods. These sensors basically consist of quantum detectors (QDs) immobilized by a linking molecule (linker) to an electrode, so that upon their illumination, a photocurrent is generated which depends on the type and concentration of the respective analyte in the immediate environment of the electrode.

The term "magnetic based" visual marker refers to a magnetic bead conjugated to a binding compound, such as an antibody, to allow detection. Magnetic particles commonly consist of magnetic elements such as iron, nickel and cobalt and their related chemical compounds. The magnetic nanoparticles are typically smaller than 1 micrometer in diameter (typically 5-500 nanometers), the larger microbeads are 0.5-500 micrometer in diameter. The magnetic nanoparticles possess attractive properties, which can be used in nanomaterial-based catalysts, biomedicine, and magnetic particle imaging.

In some embodiments, contacting of the target by the first binding compound can be performed on a solid support (see e.g. illustration of FIG. 1). In some embodiments, the contacting can be performed within a liquid medium which can be combined with the sample and then placed on a solid medium (see e.g. illustration of FIG. 3). In some embodiments, the support can be comprised of a textile strip such as nylon or cellulose, or a polymer gels or beads. In some embodiments the liquid medium can be a hydrophilic solution such as a buffer including salts and other analytes allowing maintenance of the conformation of the target and allowing binding with a corresponding binding compound.

In some embodiments the sample or liquid medium once placed on the solid support move on the solid support by lateral flow. The lateral flow technology is identifiable by a skilled person and is typically performed on porous paper or a porous support that can transport fluid. For example, a first element of lateral flow can act as a reservoir to hold a sample fluid with molecules of interest. A fluid can migrate to a second element, where the second element can be a conjugate pad that can have a first conjugate element bound to it. For example, a conjugate pad can contain a dried format of a bio-active binding agent, an antibody, or other chemical binding partner that can be dissolved in a salt-sugar matrix and can be immobilized on the surface of the conjugate pad. The sample fluid containing the target molecule can flow to the second element and can dissolve the salt-sugar matrix, it can also dissolve the second element and in a transport action of the fluid, the sample containing the target can mix and bind with the second element while flowing through the porous structure. The target can bind to the elements of the second reservoir forming a complex while migrating further through the support. The support can have one or more areas and can be called stripes where a third element, or molecule can be immobilized. When the sample containing the complex reaches the stripes, the third 'capture' molecule on the stripe can bind the complex. When more fluid has passed the stripes, the complex can accumulate and the stripe-area can change color and can be a signal for the detection. There can also be at least two stripes: one can be a control that can capture any particle in the transport fluid and can show that a reaction condition and technology worked fine, a second stripe can contain a specific capture molecule and can only capture those particles onto which an analyte molecule has been immobilized. After passing these reaction zones the fluid can enter the final porous material, the wick that can act as a waste container. Lateral flow tests can operate as a "competitive assay" or a "sandwich assays."

The lateral flow test as a "competitive assay" can refer to having as a label a colored particle or other nanometer sized particles such as gold and can be bound to an antibody. In some embodiments, the gold particles can be red in color due to localized surface plasmon resonance, or blue or red depending on the aggregation state of the particles. Fluorescent or magnetic labeled particles can be used to track target of interest, and such particular method can require the use of an electronic reader to assess the test result.

The lateral flow test as an "immunological sandwich assay," can refer to the sample that can first encounter an analyte or biomolecule such as an antibody that is raised to the target in the sample. The said analyte or biomolecule can be labeled with a colored particle so the target can be tracked in the sample. The target and the analyte in the sample can form a complex, and the complex can diffuse to a test region through lateral flow. The test region can be a second encounter for the complex and can be a line that will also contain antibodies to the same target, and it can bind to a different epitope to the target in the sample. The second antibody on the test region can also bind to the complex of labeled antibody and target. The test line can show as a colored band in positive samples when it captures the complexes that flow through the test region, and can be regarded as a signal. In some embodiments the signal can be a colorimetric indication given upon binding to the chemically reactive lines or stripes.

In particular, according to an exemplary embodiment of the present disclosure using lateral flow a device that incorporates a support comprised of a textile support wherein the support can be selected from a material composed of cellulose or nylon and can be used for identification of biomolecules. The device can be used for a lateral flow assay for the detection of targets, and can be carried out on various mediums or solutions. The devices methods and systems herein described can allow in some embodiments a quick and easy detection for presence and identification of specific biomolecules and provide a quick result than those obtained using other biodiagnostic devices and techniques. A skilled person will be able to adapt the above description of embodiments related to lateral flow to other forms of fluid movements on supports herein described, as well as related additional tests, materials and assays upon reading of the present disclosure.

In various embodiments described herein, including but not limited to embodiments wherein the devices methods and systems operate through lateral flow of a medium on a solid support, the medium can be a bulk solution or a buffer that is optimized to ensure stability of the sample (e.g. a human bodily fluid) and to preserve the biomolecules such that the binding of the primary and secondary binding compounds are not affected. In the present disclosure, the medium can be a carrier solution that is mixed with the bodily fluid to put onto the support of the detection device. The medium can be a buffer that is formulated to preserve the binding activities of biomolecules under experimental conditions and can also preserve the stability of the visual marker or label in such conditions. The buffer can be composed of but not limited to universal buffers used in biochemistry such as MES, Bis-Tris, Bis-Tris Propane, PIPES, MOPS, HEPES, and in pH values that allow stability of the said binding compounds and labels. In some embodiments, salt concentrations can be adjusted to ensure stringency of the detection and the proper preservation of the elements in the solution and the salt concentrations can range from 50 to 200 mM. Formulation of the buffers is dependent on the labels to ensure their stability and can be determined by a person skilled in the art.

In the embodiments described the medium reach the reservoirs comprising the primary or secondary binding compounds the catching or capturing of the compound or complex comprising the label by the chemically reactive line can create a positive indication of the presence of the target.

Figure 4:
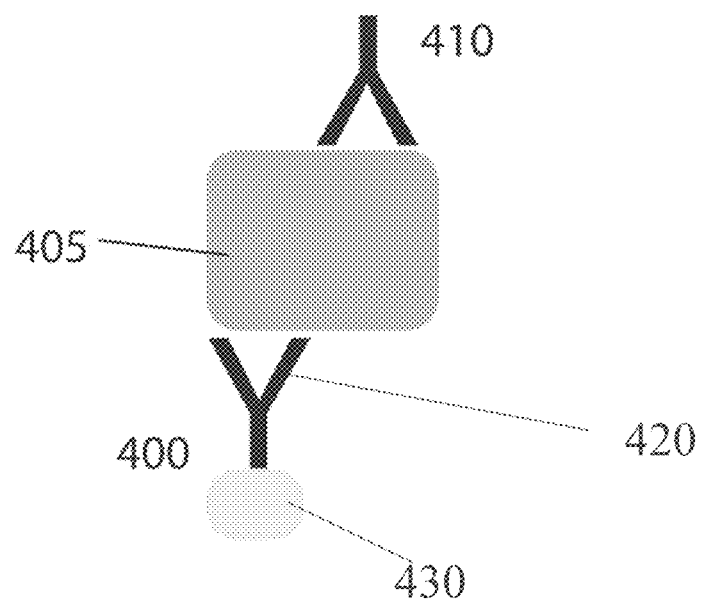
FIG. 4 depicts a schematic of an antibody that has bound and captured a target molecule with a bound antibody conjugated to a visual marker

Reference is made to the schematic illustration of FIG. 4 which depicts a capture of the target (405) by an antibody (420) that is conjugated to a visual marker (430) at a distinct site on the target (405) forming a complex. In FIG. 4, the complex formed by the target (405) and the antibody (420) is captured by a second antibody (410) on a site on the target (405) that is distinct from the first antibody binding site (400) and does not compete for the same site or epitope. In particular, in the illustration of FIG. 4, it is schematically shown that the primary compound (420) can contact a distinct site or epitope on the target (405) and bind the target (405), forming a complex. The complex formed by antibody (420) with label (430) and the target (405) is captured by a secondary compound, which can be an antibody (410), on a site or epitope on the target (405) that is distinct from the first antibody binding site, and thus forming a complex (400). Detectable targets can include proteins secreted by the bacteria into the bodily fluid that can be detected. Targets can be but are not limited to secreted metabolic factors, sugars, ligands, and additional targets identifiable by a skilled person.

In some embodiments, exemplified in the schematics of FIG. 4 the second binding compound (410) can specifically bind to the target (405) by contacting the target at a second specific epitope to which the second binding compound (410) can have a high binding affinity and not compete with the first primary binding compound (420). In particular in some of these embodiments, the second binding compound (410) can specifically recognize the target-primary compound complex and can only bind the target-primary compound complex specifically and not competitively.

Figure 5:
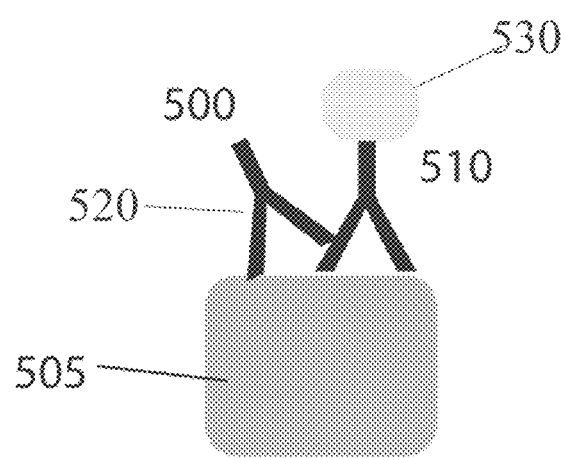
FIG. 5 depicts a schematic of an antibody that can specifically bind a complex and captures a target molecule with a bound antibody conjugated to a visual marker.

In some embodiments, the second antibody can be raised to contact and recognize a complex composed of the target and first binding compound as exemplified in the schematics of FIG. 5.

In the illustration of FIG. 5, a schematic illustration is shown exemplifying a capture of the target (505) that is complexed to an antibody (510) with a label (530) to form a complex. In the schematics of FIG. 5, the complex formed by the antibody (510) with label (530) and the target (505) is specifically captured by an antibody (520) that can only recognize the target if the target is initially complexed to the first antibody (510) thus forming a complex (500). In the device schematically illustrated in FIG. 5, the first antibody (510) attaches a label (530) which can be a visual marker.

In some embodiments, the secondary binding compound can be a molecule or antibody that can only recognize, and contact the target that is complexed to the first binding compound. The secondary compound is a capture agent and in some embodiments, can be an engineered synthetic antigen binder (sAB) or an antibody specifically raised against a complex, and can recognize the complex formed from the sample biomolecule and the first antibody of the assay. Such techniques have been described for the production of antibodies against conformation-specific proteins and complexes. For example, to obtain an sAB, to preferentially bind a complex, a phage display strategy can be carried out against the complex of interest, with and against the biomolecule alone. The term "phage display" as described herein is a technique that can be used to find a binding compound to a specific molecule and refers a laboratory technique detect protein—protein, protein—peptide, and protein—DNA interactions and uses bacteriophages to connect proteins with the genetic information that encodes them. Phage display enables libraries of proteins to be screened and amplified in a process called in vitro selection. Phage display provides a direct physical link between phenotype and genotype. Because of the ease and rapidity of DNA sequence analysis, selected molecules can be identified quickly. The bacteriophages that can be used in phage display are M13, T4, T7, and λ phage have also been used. Phage display can be used to create binding capture targets that are specific to recognize an epitope for contacting and binding. The techniques for phage display to find a binding compound is apparent to one skilled in the art.

In some embodiments the label can be a visual marker and the signal can be a visual signal. In particular, the signal can be a colorimetric indication given upon binding to the chemically reactive lines or stripes.

According to an exemplary embodiment of the present disclosure the detector, methods and systems herein described can be used for qualitative (yes/no answer); semi-quantitative (−/+/++/+++/++++) or quantitative detection of one or multiple targets. By way of example and not of limitation, the present disclosure refers to a colorimetric signal from the concentration of visual markers that are present at the secondary reservoir that can be comprised of lines or dots.

In the embodiments described herein, the support or solid medium can be comprised within portable devices. The term "mobile," "hand-held" and "portable" as used herein indicates that the device is small and an easily portable device. In the embodiments described herein, the dimensions of the device can be for example 5.02×2.58×0.39 inches and can be up to 7.87×5.3 inches×0.28 inches.

In the embodiments described herein, the embodiments can be disposable. The term "Disposable" as used herein indicates that the test is of low cost and contains materials such that it can be thrown away through traditional channels after an individual use.

In some embodiments, detectors and related methods and systems herein described can be directed to detection of a target that can be a biomolecule and in particular a biomarker detected as indicators of normal biological processes, pathogenic processes, or pharmacologic responses. In particular, detectors and related methods and systems herein described can be used for quantitative or qualitative detection of biomarkers that can be associated to pollution or microbial contamination of an environment (e.g. water pollution) or material including food and pharmaceutical preparation as well as a biological state of an organism. In some embodiments the detector and related methods and systems herein described can be used to qualitatively and/or quantitatively detect a biomarker that is produced by an organism and associated with a physiological or pathological state of the organism or parts thereof (e.g. an antigen or antibody as well as a produced metabolite or by-product of metabolism).

In particular, in some embodiments, devices methods and systems herein described are directed at the detection of biomolecules in a sample of bodily fluid, wherein the said bodily fluid can be blood, saliva, vaginal fluid and urine. In some of those embodiments, detection of biomolecules can be performed for detecting and in particular diagnosing a condition in an individual.

The term "condition" as used herein indicates a physical status of the body of an individual (as a whole or as one or more of its parts), that does not conform to a standard physical status associated with a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Four main types of disease comprise: pathogenic disease, deficiency disease, hereditary disease, and physiological disease. Diseases can be caused by factors originally from an external source, such as infectious disease, or it can be caused by internal dysfunctions, such as autoimmune diseases. Diseases can also be classified as communicable and non-communicable disease. Some diseases can be transmitted sexually and are referred to as sexually transmitted diseases. The term "infection" refers to the invasion of a host organism's bodily tissues by diseasecausing organisms, their multiplication, and the reaction of host tissues to these organisms and the toxins they produce. Infections can be caused by microorganisms such as prions, viruses, bacteria, and viroids, and larger organisms like macroparasites and fungi.

The term "individual" as used herein in the context of treatment includes a single biological organism, including but not limited to, animals and in particular higher animals and in particular vertebrates such as mammals and in particular human beings In some embodiments are directed at the detection of biomolecules in a sample of bodily fluid and can be used to diagnose a sexually transmitted disease or STD in an individual.

The wording "Sexually transmitted diseases" or "STDs", also known as sexually transmitted infections (STIs), or venereal diseases indicates infections generally acquired by sexual contact. The organisms that cause sexually transmitted diseases can pass from person to person in blood, semen, or vaginal and other bodily fluids. Examples of STDs include but are not limited to Chlamydia, Cancroids, crabs (pubic lice), Genital Herpes, genital warts, Hepatitis B, HIV/AIDS, Human Papillomavirus (HPV), Trichomoniasis (parasitic infection), Pelvic Inflammatory Disease (PID), Syphilis, Gonorrhea, Trichomoniasis (Trich), and Yeast infections.

In some embodiments, STDs diagnosable with the support, devices, methods and systems herein described can include yeast infection, trichomoniasis, bacterial vaginosis, Herpes simplex, Hepatitis HCV, Chlamydia, Gonorrhea, and Syphilis. In some embodiments, the target detectable with a support, device, methods and systems herein described can include for example toxins such as endo- or exotoxins, thermostables or thermoliable. Examples of mycotoxins are aflatoxins type A & B, oxchratoxin. In some embodiments, targets detectable with a support, device, methods and systems herein described can also include residues of pesticides and can be PCB, dithiocarbanates, propamocarbe, benzimidazoles, and organocholides.

In some embodiments, targets detectable with a support, device, methods and systems herein described can include residues of antibiotics from beta-lactams, tetracyclines, macrolides, quinolones, sulfonamides, aminoglycosides but also antibiotics that are used as animal growth promoters such as bacitracin, tylosin, spiramycin, virginiamycin, and avoparcin. In some embodiments, targets detectable with a support, device, methods and systems herein described can include a virus or a molecule associated thereto (e.g. a virus from virus family: adenoviridae, coronoviridae, papovaviridae, retrovoviridae, and additional families identifiable by a skilled person) a bacterium (e.g. Yersinia, Aeromonas, Pasteurella, Vibrio, Helicobacter (H. pylori) species, and additional bacteria identifiable by a skilled person) and/or molecules associated with the diagnosis of acute phase proteins (e.g. rheumatoid factors, CRP, serum amyloid, A, and additional molecule identifiable by a skilled person). In some embodiments, target detectable with a support, device, methods and systems herein described can include HIV (human immunodeficiency virus) and the detection can be performed to diagnose AIDS. Examples of targets which can be detected with a support, device, methods and systems herein described are methamphetamine, barbiturates, benzodiazepine, amphetamine, morphine, THC, cocaine and profile.

In various embodiments described herein, detection of biomolecules from a sample of bodily fluid wherein the fluid can be vaginal fluid or urine are described, wherein the target biomolecule is a biomarker for a sexually transmitted disease (STD).

In accordance with the present disclosure, in the embodiments described herein, the target biomolecule or biomarker of an STD can be for example first targeted by an IgG antibody, which can be the primary binding compound of the STD biomarker.

In some embodiments, detectors, methods and systems herein described, can be used to detect biomarkers of common STDs: trichomoniasis, bacterial vaginosis, Herpes, Chlamydia, Syphilis and Gonorrhea.

In the various embodiments described herein, detection of biomolecules in a sample for diagnosing an STD in an individual are described by use of a lateral flow device, specifically a device described above as an immunological sandwich, wherein the sample is a bodily fluid, and the first binding compound or capture agent is an IgG antibody comprising a visual marker as a label, and the second capture agent is an IgG antibody.

Exemplary embodiments are described herein that use a pH test on the support in the detection of an STD. By way of example and not of limitation, the present embodiments describes the pH strip of the substrate as comprising a simple litmus type material and can react colorimetrically with solution to indicate the approximate solution pH. The pH test can be used to aid in a diagnosis. A "pH indicator" is a usually a litmus paper that can be used to measure pH, wherein there can be a color change with pH. A visual comparison of the color of a test solution on the indicator with a standard color chart can provide a mean to measure a pH accurately to the nearest whole number. Precise measurements can be possible when the color is measured spectrophotometrically, using a colorimeter of spectrophotometer. Universal indicator consists of a mixture of indicators such that there is a continuous color change from about pH 2 to pH 10. Indicator paper can be made from an absorbent porous paper that has been impregnated with a universal indicator. By way of example and not of limitation, the use of a pH measurement can be applied to medicine, biology, chemistry, agriculture, forestry, food science, environmental science, oceanography, civil engineering, chemical engineering, nutrition, water treatment, water purification, and many other applications.

In some embodiments, the detection of a pH of the vaginal secretions can be used in several embodiments to determine an elevated pH (i.e., >4.5) which can be common with bacterial vaginosis or trichomoniasis, and can be detected by using a narrow-range pH paper. In some embodiments describe pH tests for testing vaginosis and trichomoniasis in human bodily fluid.

Assembly of a device in accordance with the present disclosure can be implemented in a variety of ways. A few example implementations include: a support with a first reservoir or support portion for an initial or first binding compound, a series of secondary reservoirs or support portions for a second binding compound, a third reservoir or support portion with reagents to bind the medium components as a control, and a pH indicator; a support with a first reservoir or support portion for an initial or first binding compound, a series of secondary reservoirs or support portions for a second binding compound that are staggered in their position on the support, a third reservoir or support portion with reagents to bind the medium components as a control, and a pH indicator; a detection device with a support for immersion that contains a buffer solution with a first binding component to the target, the second binding compound on the support, a third reservoir with reagents to bind the medium components as a control, and a pH indicator.

In some embodiments, detectors, and related methods and systems can comprise a portable disposable support, to detect biomolecules indicative of a specific sexually transmitted disease (STD) in an individual. According to an exemplary embodiment of the present disclosure, a structure similar to the schematic of FIG. 1 and FIG. 2 is described that can be used to test for at least one STD on a mobile support. The mobile support can comprise a first reservoir or support portion on the support containing primary binding compounds comprising a label that is specific to bind a target biomolecule, chemically reactive lines or dots on said support that are representative of the secondary reservoirs depicted in FIG. 1 and FIG. 2 that contain a secondary binding compound, and a medium comprising a carrier solution that can contain the biomolecules, wherein said lines or dots containing the secondary binding compound on the textile strip can react with the biomolecules in the carrier solution that have complexed with the primary binding compounds in the first reservoir or support portion and have been brought to them by lateral flow of the carrier solution, and wherein the reaction of the applied biomolecules in solution plus the reagents on the strip causes as signal, such as a line to be visualized if the biomolecules applied to the strip contain targets that the device is designed to test. For example, the secondary reservoirs or support portions can be arranged in a row as depicted in FIG. 1, or can be staggered to prevent a cross reaction as depicted in FIG. 2. Such device can also contain a support region for a control test for the components in the medium, pH indicator and can include an assay based on pH measurements.

In some embodiments, the secondary reservoirs as depicted in FIG. 1-2, or the first reservoir as depicted in FIG. 3, can take the form of chemically reactive lines or dots which can contain compounds that can bind to the target-compound complex. Chemically reactive lines or dots as described in the present disclosure can refer to a structure on the said support that is formed by the spotted down chemistries. "Spotted down chemistries" as described in the disclosure refers to a mixture, solution, or sequence of mixtures and/or solutions applied to the "test strip material" which therein comprises a target binding compound such as the primary reservoir, secondary reservoir, pH indicator, or pH control strip. The chemically reactive lines or dots are not limited in shape to lines or dots. The chemically reactive lines or dots can be formed for example by any combination of squares, rectangles, triangles, ellipses, heptagons, hexagons, and octagons.

In some embodiments, the secondary binding compound can be a molecule that has been covalently attached to the support and can bind the target that is bound to the first binding compound that comprises the visual label. By way of example and not of limitation, the secondary compound can be an antibody and in particular an IgG antibody.

In some embodiments, detectors and related methods and systems herein described comprise an immersion detection device to detect specific biomolecules indicative of a specific sexually transmitted disease (STD) can have the reservoir or support portion that captures the target-primary compound complex as exemplified in FIG. 3. In those embodiments, the medium or carrier solution (330) can contain the primary binding compounds with the target molecules associated with one or more STDs. The applied carrier solution can be brought to the reservoirs or support that contain the secondary binding compounds by lateral flow of the carrier solution, and wherein the reaction of the applied biomolecules in solution plus the reagents on the strip causes as signal, such as a line to be visualized if the biomolecules applied to the strip contain targets that the device is designed to test. Such device can contain control strips that react with the medium or carrier solution. Such device can also contain a pH indicator and can include an assay based on pH measurements.

In some of those embodiments, an immersion device is described that has a support portion containing an IgG antibody against a complex that is formed in a buffer solution with STDs biomarkers possibly presented in a human bodily fluid. The term "immersion" as used herein refers to the ability of the device to be submerged at least in part in a solution. By way of example and not of limitation, the present disclosure describes an immersion device that can be placed in a medium containing the said bodily fluid and a first binding compound optionally together with a buffer or an additional vehicle.

Figure 6:
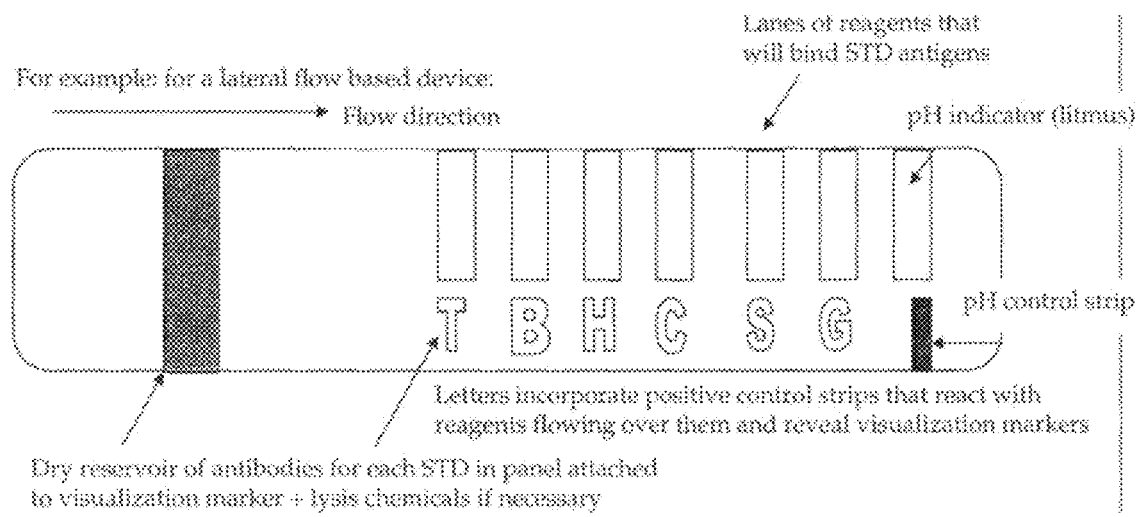
FIG. 6 shows a schematic illustration of devices, methods and systems, according to an embodiment herein described
Figure 7:
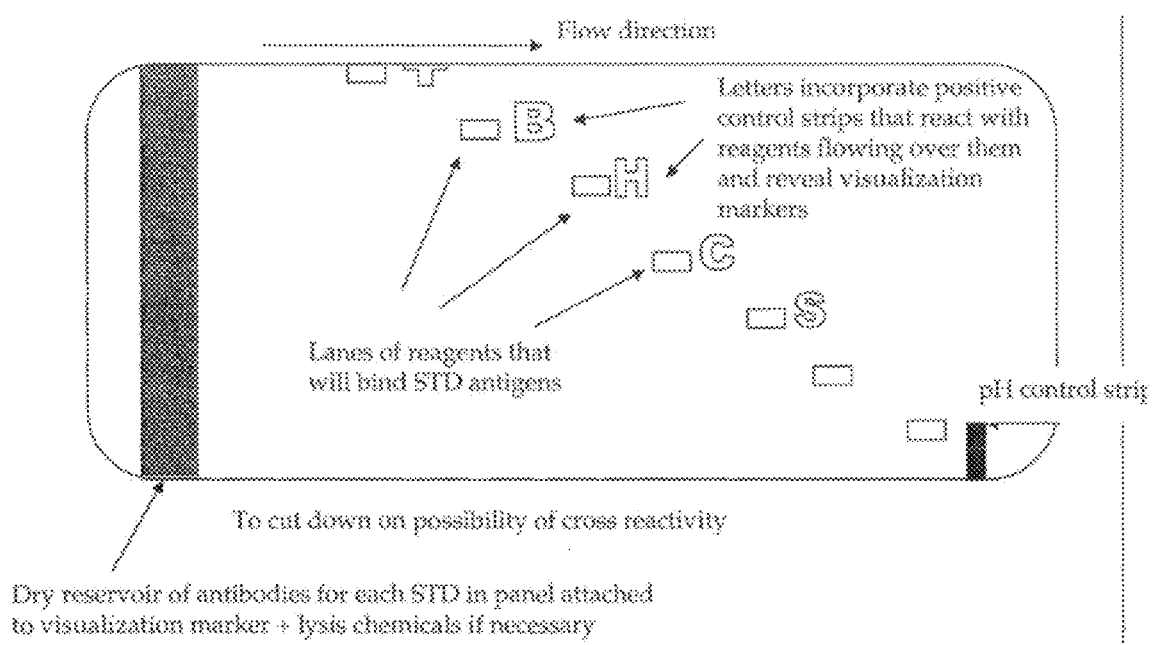
FIG. 7 shows a schematic illustration of devices, methods and systems, according to an embodiment herein described
Figure 8:
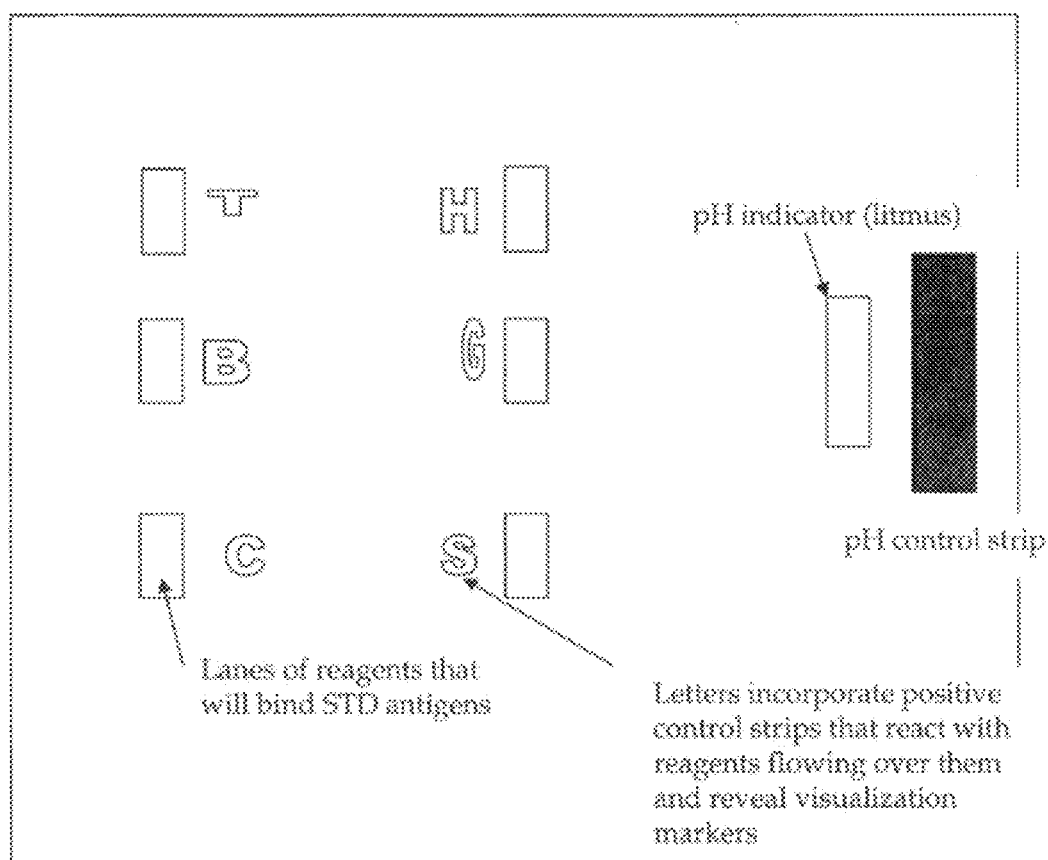
FIG. 8 shows a schematic illustration of devices, methods and systems, according to an embodiment herein described

According to an exemplary embodiment of the present disclosure, the control strip on the support of the detection device can react with the medium or buffer used for the lateral flow and can be presented as shapes such as alphabetical letters on the support as shown in the schematic illustration of FIGS. 6 to 8. The control strip can contain antibodies that can bind to the unbound primary binding compound and produce a signal.

In some embodiments a method of detecting molecules from a support comprises combining a bodily fluid with a liquid medium that allows binding reactions to occur, applying the labeled complex to one side of a support that allows fluid to be drawn through bringing the complex across the support by lateral flow, combining the complex with a second binding compound specific to the target, and deriving information pertaining the target molecule via a visual signal, wherein the signal comprises a visual detection selected from an increased concentration of colloidal particles, colloidal gold, colloidal magnetic particles, colloidal quantum dots.

According to an exemplary embodiment of the present disclosure, the bodily fluid can be placed within a medium such as a buffer to preserve its binding activity and native form of molecules in the said buffer or solution, prior to placement of the immersion detection device, so that a set amount of volume can be wicked through the device.

According to an exemplary embodiment of the present disclosure, the method can further comprise placing the buffer directly onto one side of the support. The support can wick the amount of fluid containing the biomolecules to draw through them through the support into the first and second support portions.

According to an exemplary embodiment of the present disclosure, the method of using the support can also include mixing of the buffer with bodily fluid at the first support portion and dissolving the dried first binding compound and forming a complex. The complex can then travel by lateral flow to the second support portion. The concentration of targeted biomolecules at the second support portions can elicit a signal due to the increased concentration of labels such as colloidal particles, colloidal gold, colloidal magnetic particles, or colloidal quantum dots. The time that the lateral flow can occur to produce a result can vary with the size of the support and can range from five to ten minutes.

In some embodiments, detecting molecules from a detection device can comprise combining a bodily fluid with a first binding compound specific to a target and comprising a label to form a complex in a liquid medium that allows binding to occur, and applying the labeled complex to one side of a support that allows fluid to be drawn through bringing the complex across the support by lateral flow. The method can further comprise combining the complex with a second binding compound specific to the target, and deriving information pertaining to the target molecule via a signal such as a visual signal, wherein the signal comprises a visual detection selected from an increased concentration of colloidal particles, colloidal gold, colloidal magnetic particles, colloidal quantum dots.

According to an exemplary embodiment, the method of using an immersion device comprises, mixing or combining the bodily fluid with the medium or buffer that can contain a binding molecule that comprises a colloidal label such as colloidal gold, magnetic particle, or quantum dots. Buffer can be optimized to ensure binding activity and preservation of biomolecules and binding compound. The buffer containing the bodily fluid and binding material can then be introduced to the detection device by immersion to allow the medium or buffer to flow through the device by lateral flow wherein the bound complex is then captured by the support portions that contain a binding compound that specifically targets the complex. A visual signal can be used to detect the specific molecule bound as the concentration of the complex is increased.

By way of example and not of limitation, the first binding compound of the immersion device can be an IgG antibody conjugated to a colloidal label, wherein the colloidal label can be selected from colloidal gold, colloidal magnetic particle, and colloidal quantum dots.

By way of example and not of limitation, the buffer medium can be used at volume that allows submersion of the device and the device can be allowed to be immersed in the solution of buffer containing the bodily fluid and the first binding compound.

In some embodiments, after immersion of the detection device, the colorimetric signal can be read after ten to fifteen minutes. By way of example and not of limitation, the label can be colloidal gold, and a red color can be seen at the secondary support containing the secondary binding compound if there is a positive test.

In some embodiments, a support herein described can be manufactured by: treating of a support to allow lateral flow of fluids, creating a solution for applying the primary binding compound to the primary reservoir of the support to preserve the binding activity, applying a primary reservoir on the support to maintain the chemical or molecule in a form for binding, and applying the primary binding component to maintain a binding capability in a preserved format. The method can further comprise applying a secondary reservoir on a support for a secondary binding compound, creating a solution for applying the secondary compound to maintain the integrity of the secondary compound on the support, and applying a secondary binding compound onto the support in a solution to maintain the binding capabilities. The method can also comprise applying a control reservoir with reagents to bind to a carrier medium in a preserved format, and creating a reservoir for a pH litmus indicator for a solution carrying biomolecules creating a reservoir for a pH test for a solution carrying biomolecules.

According to an exemplary embodiment of the present disclosure, the support can be sterilized and treated with protease inhibitors to ensure that proteases on the support are minimized. In some embodiments, the primary binding compound can be a dried lyophilized antibody that is placed onto the primary reservoir. In some embodiments, the secondary binding compound can also be in a dried format and is placed such that it can be covalently bound to the support.

The method of manufacturing the support further comprises lyophilizing the chemical binding partners for the support and dissolving in a salt-sugar matrix so they can be applied to the support.

In some embodiments, a detection device can be manufactured by treating of a support to allow the lateral flow of fluids, creating a solution for mixing the primary binding compound to the solution sample to allow binding of compounds, applying a reservoir on the support to maintain the chemical or molecule in a form for binding, applying the binding component to maintain a binding capability in a preserved format, applying a secondary reservoir on a support for a secondary binding compound, creating a solution for applying the secondary compound to maintain the integrity of the secondary compound on the support, applying a secondary binding compound onto the support in a solution to maintain the binding capabilities, applying a control reservoir with reagents to bind to a carrier medium in a preserved format, creating a reservoir for a pH litmus indicator for a solution carrying biomolecules creating a reservoir for a pH test for a solution carrying biomolecules.

The method of manufacturing a detection device can further comprise treating the support with a protease inhibitors as well as sterilization to prevent the degradation of proteins during the assay by any proteases. The method of manufacturing the detection device can further comprise lyophilizing the chemical binding partners for the support and dissolving in a salt-sugar matrix so they can be applied to the support.

As described herein, the support, binding compounds, and mediums of the disclosure can be provided as a part of systems to perform any assay, including any of the assays described herein. The systems can be provided in the form of kits of parts. In a kit of parts, the binding compounds, mediums and other reagents to perform the assay can be comprised in the kit independently. The binding compounds which can be labeled or not can be included in one or more compositions and each binding compound can be in a composition together with a suitable vehicle.

Additional components can include labels or labeled molecules and in particular, labeled polynucleotides, labeled antibodies, labels, microfluidic chip, reference standards, and additional components identifiable by a skilled person upon reading of the present disclosure.

In some embodiments, detection of a binding compound of the disclosure can be carried either via fluorescent based readouts, in which the labeled antibody is labeled with fluorophore, which includes, but not exhaustively, small molecular dyes, protein chromophores, quantum dots, and gold nanoparticles. Additional techniques are identifiable by a skilled person upon reading of the present disclosure and will not be further discussed in detail.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

In some embodiments, a kit can comprise at least one plastic platform to hold a support, at least one support structure, at least one small primary support portion containing at least one molecule covalently bound to a visual colloidal marker, a plurality of secondary support portions comprising secondary binding compounds that are covalently bound to the support portions and chemically active, at least one pH litmus indicator, at least one pH strip, and a buffer for lateral flow on the porous membrane support that allows preservation and activity of binding compounds.

In some embodiments, the kit or other detectors, methods and systems herein described comprise a disposable device for performing bio-diagnostic tests upon flowing fluids.

In some embodiments, detectors, methods and systems herein described can be used in alternative or in addition to additional diagnostic techniques such as nucleic amplification, fluorescent staining and culturing as well as wet mount, whereby, for example, a sample of the bodily fluid can be placed on a glass microscope slide and mixed with a salt solution, and then examined under a microscope for bacteria, as well as detection of yeast cells, trichomoniasis organisms (trichomonads), white blood cells which can also be used to indicate an infection.

In some embodiments, detectors, methods and systems herein described provide an available, disposable, easy to read, real-time technology today, that enables individuals to quickly and easily test for STDs as well as for other detections where for example short-lived proteins are to be measured. In some embodiments, detectors, methods and systems herein described provide a rapid on site test in a public clinic that can offer potential advantages to the current testing strategies. In particular in some embodiments, patients are expected to receive their results and result specific counseling on the day of the initial visit, and to reduce the need to return for a visit for a negative test.

The devices methods and systems herein described are further illustrated in the following examples, which are provided by way of illustration and are not intended to be limiting.

EXAMPLES

The detector, methods and systems herein described are further illustrated in the following examples, which are provided by way of illustration and are not intended to be limiting.

The methods and devices for detecting a biochemical or biomarker in a sample, related supports, and a method and/or device using assays herein disclosed are further illustrated in the following examples, which are provided by way of illustration and are not intended to be limiting. The following exemplary methods, devices and methods for biomolecule and biomarker detection are illustrated in connection with experimental procedures and with reference to STDs. A person skilled in the art will appreciate the applicability and the necessary modifications to adapt the features described in detail in the present section, to methods and devices according to embodiments of the present disclosure.

Example 1. A Method of Manufacturing a Support

A support such as support (100) of FIG. 1; support (200) of FIG. 2, or the supports illustrated in FIG. 6 and FIG. 7 can be built with a material of nylon or cellulose treated in order to allow the lateral flow of fluids. Treatment can be performed by autoclaving the material under the dry cycle of the autoclave at twenty-five minutes, and treating the material to a solution of 1% PMSF in 20% ethanol and allowing to air-dry. After this treatment, a buffer that is expected to comprise Tris-HCl 50 mM and 150 mM NaCl containing six visually labeled IgG antibodies against biomarkers can be added. In particular, the IgG can be added specific for biomarkers of the following STDs: trichomoniasis, bacterial vaginosis, Herpes, Chlamydia, Syphilis and Gonorrhea at 1:1000 dilution each to the buffer are added at 1 ml to a first support portion (FIG. 1 (110); FIG. 2 (205); FIG. 6, "dry reservoir of antibodies"; and FIG. 7, "dry reservoir of antibodies") onto the support and allowed to dry. The regions for the secondary support portions (FIG. 1 (115); FIG. 2 (210). FIG. 6, "reagents that bind STD antigens"; FIG. 7, "reagents that bind STD antigens") can be marked off for the following diseases to detect: trichomoniasis, bacterial vaginosis, Herpes, Chlamydia, Syphilis and Gonorrhea, and can also be shown by the alphabetical lettering T, B, H, C, S, and G as shown in FIGS. 6, 7 and 8. The second support can be formatted to contain regions that have an aldehyde-active support such as the ones that are commercially available (Pall Corporation) and can be activated to covalently adhere to the specific binding compounds (the second IgG antibodies). The six antibodies that are specific to the antibody-complex are expected to be added by dissolving the antibodies in an amine free buffer such as a phosphate buffer and applying the antibodies to the aldehyde activated support portion separately at 500 uL at a concentration of 1 mg/ml. The amination involving the formation of an initial Schiff base between the aldehyde on the support and amine groups on the antibodies, which then is reduced to a secondary amine by the addition of 500 uL sodium cyanoborohydride (NaCNBH3) after an hour of incubating the antibodies.

The antibodies can be applied in a buffer that does not have free amines to avoid binding of the buffer onto the support and other amine free buffers can be used that are known to a person skilled in the art. The control regions containing six specific IgG antibodies to the first binding compound are similarly affixed to the support using an aldehyde activated support to bind the antibody covalently to the third support portion.

As shown in portion (115) of FIG. 1, (210) of FIG. 2, and "reagents that bind STD antigens" FIG. 6, and "reagents that bind STD antigens" of FIG. 7, the second support portions can be periodically spaced or they can be staggered (See portion (210) of FIG. 2; and "reagents that bind STD antigens" of FIG. 7). A third support portion can be created by affixing a pH litmus indicator to the support and can come after the plurality of the second and third support portions as seen in the figures (portion (130) FIG. 1; portion (230) of FIG. 6; "pH indicator" of FIG. 6; and "pH indicator" of FIG. 7). A fourth support portion can be placed at the end of the support and can contain the pH test strip that is comprised of litmus as shown in the figures (portion (125) of FIG. 1; portion (225) FIG. 2; "pH control" FIG. 6; and "pH control" FIG. 7).

Example 2. A Method of Manufacturing a Detection Device

A support such as the one schematically illustrated in FIG. 3, and FIG. 8 comprising a material of nylon or cellulose is expected to be manufactured by treating the material in order to allow the lateral flow of fluids and then attaching antibodies. The treating can be performed by first sterilizing and comprises autoclaving the material under the dry cycle of the autoclave at twenty-five minutes, and treating the material to a solution of 1% PMSF in 20% ethanol and allowing to dry. After which, a buffer of Tris-HCl 50 mM and 150 mM NaCl is sterilized for 45 minutes and is stored accordingly at room temperature.

The six first binding compounds can be visually labeled IgG antibodies to the six previously described STDs of Example 1, and can be kept at 1:1000 dilution and are stored at −4° C. in a solution of Tris-HCl 50 mM, 50 mM NaCl and 50% glycerol, until use. The regions for the primary support portions (region (305) of FIG. 3, "reagents that bind STD antigens" of FIG. 8) can contain six antibodies that are specific to bind the biomarkers of the six STDs and are for the following diseases to detect: trichomoniasis, bacterial vaginosis, Herpes, Chlamydia, Syphilis and Gonorrhea. As described in Example 1, the support portion of the detection device can be manufactured to contain an aldehyde-active support, which is commercially available, and is a common way to covalently attach the covalently bound second binding compound, which is the IgG antibody to capture the stable complex. Attachment of the antibody to the support can be done in a similar method of Example 1. Additional support portions that contain a covalently bound antibody against the unbound first binding compound is also added to the support as a control (FIG. 3, (310); FIG. 8, "letters incorporate positive control strips") similarly to the aldehyde activated support and are marked off in their specific position on the support by alphabetical lettering as seen in FIG. 8. A third and a fourth support portion is also configured onto the device which contain a pH control strip (FIG. 3, (320); FIG. 8, "pH control strip) and a pH indicator (FIG. 3, (315); FIG. 8, "pH indicator").

Example 3. Suitable Methods to Use a Support to Detect Biomarkers of an STD

In an exemplary body of experiments, biomolecules or biomarkers for STDs are expected to be detectable using the following methods. Urine or vaginal fluid can be prepared in order to detect STDs. For vaginal fluid, the fluid can be collected using a fluid absorbent medium or a commercially available product, Instead SoftCup, wherein the fluid can be extracted for medical diagnosis. For the urine sample, approximately thirty milliliters can be collected for the detection.

Following collection at room temperature, the fluid is then mixed with the buffer which can have a working pH between 7.2 and 8.5, wherein the buffer is composed of 50 to 100 mM of a buffer for biochemical reactions selected from the following compounds Tris, Tris-HCl, Bis-Tris, Bis-Tris Propane, MES, MOPS, HEPES, and PIPES. Salt concentration for NaCl can range between 50 mM to 150 mM for stringency conditions of binding. The urine sample at thirty milliliters can be mixed with the buffer in a 1:1 volume/volume ratio. For the vaginal fluid, the extracted fluid can be mixed with approximately twenty-five milliliters of buffer. An alternative method to obtain the vaginal fluid is to soak the fluid absorbent medium in twenty-five milliliters of buffer in a specimen cup for approximately thirty minutes to an hour.

The samples prepared according to this procedure can then be used with an embodiment as shown in FIGS. 1, 2, 6, and 7 which depicts a schematic top view of several embodiments of the present disclosure. In order to detect the STD biomarkers from either the vaginal fluid or the urine sample, the buffer containing the bodily fluid is placed to the one end of the support (FIG. 1, (100); FIG. 2, (200); FIG. 6, left side of the figure; FIG. 7, left side of the figure) that is closest to the first binding portion (FIG. 1, (110); FIG. 2, (205); FIG. 6, "dry reservoir of antibodies"; FIG. 7, "dry reservoir of antibodies") on one side of a support, wherein the first binding portion contains the six IgG antibodies, that target the STDs previously described in Example 1. After placing the fluid on one side of the support, visualization of the fluid can be expected to be seen as it travels from one end of the support into the reservoirs containing the binding compounds. The first binding compounds of IgGs are comprised of visualization labels of colloidal gold that range in size of about 32.6±3 nm which emit a color of reddish-purple and flow of the colored fluid can be expected to be seen as the solution mixes and dissolves the components in the first support portion and travels through the support towards the plurality of spaced secondary binding supports (FIG. 1 (115); FIG. 2 (210); FIG. 6, "lanes of reagents that will bind STD antigens", and FIG. 7, lanes of reagents that will bind STD antigens").

As the mixture flows into the regions containing the second support portions, the specific IgG antibodies that are affixed to the plurality of second support portions can specifically capture a complex that pertains to the previously described STDs of Example 1. The target-compound complex can flow towards the second support portion where the specific target complex is captured at a specific second support portion containing an antibody to the specific target complex and the local concentration of the target-compound complex of a specific STD is increased and can be visualized because of the visual marker that is bound to the first compound and a reddish-purple line can be seen due to the colloidal gold marker. If a specific STD biomarker is not found, the free unbound IgG antibody of the first support portion can be captured with an IgG antibody that is specific to the free unbound IgG antibody of the first support portion at the third support portion (FIG. 1 (120); FIG. 2 (215); FIG. 6, "letters that incorporate positive control strips," and FIG. 7, "letters that incorporate positive control strips,") and a reddish-purple line can be seen. If there are no biomarkers detected in the liquid, the reddish purple line can be expected at the control support portions, which contain antibodies against the free first binding antibody. However, for example if the liquid transporting the bodily fluid contains biomarkers for the STDs Syphilis and Gonorrhea, one would expect to see a concentration of a colorimetric signal at the specific secondary support portion containing the second binding antibody to the biomarkers of Syphilis and Gonorrhea.

However, as there is an excess of first binding compound in the first support portion, the control should always have a color exhibited as the solution flows through the support as a positive control to indicate that the assay is working correctly. According to an exemplary embodiment of the present disclosure, the control strips can be shapes such as alphabetical letters of T, B, H, C, S and G, which refer to the STDs of trichomoniasis, bacterial vaginosis, Herpes, Chlamydia, Syphilis and Gonorrhea, respectively, and visually indicate what the following supports are specifically detecting (FIG. 6 and FIG. 7). Finally, the solution can then flow to the pH strip and show the pH of the solution for indication of either bacterial vaginosis or trichamonas (FIG. 1, (125); FIG. 2 (220); FIG. 6, "pH control strip"; FIG. 7, pH control strip).

Example 4: Suitable Methods to Use a Detection Device to Detect Biomarkers of an STD with a Support that Uses Immersion In an exemplary body of experiments, biomolecules or biomarkers for STDs are expected to be detectable using an embodiment that is shown in FIG. 3 and FIG. 8 that uses an immersion of the device into the bodily fluid sample. As previously indicated in Example 3, urine or vaginal fluid can be prepared in order to detect STDs. In comparison to the previous devices the immersion device uses more buffer and fluid as the device is immersed for the experiment. For vaginal fluid, the fluid can be collected using a fluid absorbent medium or a commercially available product, Instead SoftCup, wherein the fluid can be extracted for medical diagnosis. For the urine sample, approximately forty five milliliters can be collected for the detection.

Following collection at room temperature, the fluid is then mixed with the buffer which can have a working pH between 7.2 and 8.5, wherein the buffer is composed of 50 to 100 mM of a buffer for biochemical reactions of a buffer selected from the buffers listed in Example 3. The urine sample at thirty milliliters can be mixed with the buffer in a 1:1 volume/volume ratio. For the vaginal fluid, the extracted fluid can be mixed with approximately forty-five milliliters of buffer. An alternative method to obtain the vaginal fluid is to soak the fluid absorbent medium in forty-five milliliters of buffer in a specimen cup for approximately one to two hours, to increase the amount of biomarkers collected.

The samples prepared according to this procedure can then be used with an embodiment as shown in FIG. 3 and FIG. 8, which depicts a schematic top view of one embodiment of the present disclosure. In order to detect the STD biomarkers from either the vaginal fluid or the urine sample, the buffer containing the bodily fluid (335) is mixed with 1 mg/ml dilution of the six antibodies against the six STDs that were described in Example 1 where each antibody comprises the visualization labels previously described in Example 3. After agitation of the buffer containing the bodily fluid and antibodies for about 30 minutes to ensure complex formation, the solution is placed in a wide necked specimen cup and the detection device is placed such that the solution is touching the one end of the detection device support (FIG. 3 (300), FIG. 8) that is closest to the first binding portion (FIG. 3, (305); FIG. 8, "lanes of reagents that will bind STD antigens" wherein the first binding portion containing the six affixed IgG antibodies as described in Example 1, that target the following complexes that have biomarkers for the previously described STDs of Example 1. After placing device such that the fluid is contacting one side of the support, visualization of the fluid can be seen as it travels from one end of the support into the reservoirs containing the secondary binding compounds.

As the mixture flows into the regions containing the first support portions, the specific IgG antibodies that are affixed to the plurality of first support portions (FIG. 3 (305); FIG. 8 "lanes of reagents that will bind STD antigens") can specifically capture a complex that pertains to the specific STDs. The liquid containing target-compound complex can flow towards the first support portion (FIG. 3 (305); FIG. 8, "lanes of reagents that will bind STD antigens") where the specific target complex is captured at a specific first support portion containing an antibody to the specific target complex and the local concentration of the target-compound complex of a specific STD is increased and can be visualized because of the visual marker that is bound to the first compound and a reddish-purple line can be seen due to the colloidal gold marker.

As previously described in Example 3, if a specific STD biomarker is not found, the free unbound IgG antibody that was mixed in the buffer with the human bodily fluid can be captured at the control portion (FIG. 3, (310), FIG. 8, "positive control strip) and a reddish-purple line can be expected as previously described in Example 4. However, for example if the liquid transporting the bodily fluid contains biomarkers for the STDs Herpes and Gonorrhea, one would expect to see a concentration of a colorimetric signal at the specific secondary support portion containing the second binding antibody to the biomarkers of Herpes and Gonorrhea.

According to an exemplary embodiment of the present disclosure, the control strips can be shapes such as alphabetical letters as previously described in Example 3 (FIG. 3 and FIG. 8). Finally, the solution can then flow to the pH strip (FIG. 3 (315), FIG. 8, "pH strip") and show the pH of the solution for indication of either bacterial vaginosis or trichamonas.

Example 5: Method of Attaching a Magnetic Particle to an Antibody

An antibody labeled with a magnetic particle is expected to be prepared as follows. Carbodiimides, are reagents that can be used to covalently link an amine and a carboxyl containing molecule. Carbodiimides activate carboxyl groups, and the activated intermediate is then attacked by an amine (e.g. provided by a lysine residue on an antibody). Carbodimides are commonly used to conjugate antibodies to carboxylated particles (e.g. latex particles, magnetic beads), and to other carboxylated surfaces, such as microwell plates or chip surfaces. Carbodiimides can be used to attach dyes or protein labels to antibodies.

For the method, N-ethyl-N-(3-dimethyl aminopropyl) carbodiimide hydrochloride (EDC, 26 mM) and 10 mM N-hydroxy succinimide (NHS) are dissolved in 0.1 M 2-(N-morpholino) ethane sulfonic acid (MES) buffer (pH=8.3). The mixture is added to 1 ml of 5 mg/ml nanomag 20 nm nanoparticles, and shaken at room temperature for 2 hours. The particles are washed twice with phosphate buffered saline (PBS) pH=7.4 and then 0.5-1 mg/ml of the IgG was added to the activated particles. The mixture is shaken for 3 hours and the reaction was quenched by the addition of glycine for 30 minutes. The unconjugated antibodies are separated from conjugated antibodies by gel filtration, and one would expect that you would obtain multiple peaks in the chromatogram conferring antibodies that are unbound and antibodies that are bound.

Example 6: Method of Attaching a Gold Particle to an Antibody

An antibody labeled with a gold particle is expected to be provided as follows. Optimal concentration of an antibody for conjugation can be determined by titrating aliquots of diluted antibody with colloidal gold nanoparticles (AuNPs). The purified antibody is diluted to a concentration of 0.1 mg ml$^{-1}$ in phosphate buffered saline (PBS) buffer (0.001 M, pH 7.4). The pH of colloidal gold solution and the diluted antibody is then adjusted to pH 8.0 with 0.1 N NaOH. Ten aliquots of variable concentrations (0.01-0.1 mg ml$^{-1}$) of the diluted antibodies are to be prepared in 0.1 ml PBS buffer, and added separately to 1 ml of colloidal gold solution. The tubes are incubated for 15 min and 0.1 ml of 10% NaCl is then added. The UV-visible absorbance is then recorded and estimated at the wavelength of around 523 nm. The least amount of protein required to sufficiently bind to the colloidal gold is determined from the curves of the absorbance.

After determining the optimal concentration of binding antibody, the antibody/gold nanoprobes can be prepared. For example an aliquot (50 µl) of antibody prepared in PBS (0.01 M, pH 7.4) is added slowly to 2 ml colloidal gold solution pH8 (adjusted by 1 N NaOH) followed by the addition of bovine serum albumin (BSA) (100 µl, 10%) under gentle stirring after 45 min. The mixture was incubated for another 1 h at 4° C. and then centrifuged (10 000 rpm for 15 min at 4° C.) to remove supernatant unconjugated antibody. The pellet obtained is then washed with PBS once again. The pellet is then finally redispersed in 0.5 ml PBS (pH7.4) containing 2% BSA and stored at 4° C.

Example 7: Method of Attaching a Quantum Dot Particle to an Antibody

An antibody labeled with a quantum dot (QD) particle is expected to be provided as follows. The method comprises using commercially available QDs. Qdot 655 ITKTM amino (PEG) QDs by Invitrogen are used in the conjugation with IgG antibodies.

The commercial Qdot 655 ITKTM amino (PEG) QDs are CdSe/CdS QDs having an amine-derivatized polyethylene glycol (PEG) outer coating that can react directly with amine-reactive groups, such as sothiocyanats and succinimidyl esters, or with carboxylic acids of proteins and other water-soluble biopolymers in aqueous solution using water-soluble carbodiimides, such as EDC (N-(3-dimethylaminopropyl)-N0-ethylcarbodiimide hydrochloride). The direct conjugation of Qdot 655 ITKTM to IgG antibodies through amine-carboxylic acid coupling is used with EDC (N-(3-dimethylaminopropyl)-N0-ethylcarbodiimide hydrochloride) as a catalyzer. According to the method, the QDs (10 µl, 32 nM) are mixed with EDC activated antibodies (1000, 1012 CFU in PBS) and react for 1 h at 4.0 temperature; then the mixture is agitated at 200 rpm for 1 h at 4° C. temperature. The QD-Antibody conjugates are then separated from the excess free Abs and QDs via centrifugation of 12000 rpm at 4.0 temperature in NaCl (2.5 M) solution containing 20% PEG (twice). The concentrated QD-antibody complex is then diluted in 100 µl PBS buffer.

The examples set forth above are provided to give those of ordinary skill in the art a complete disclosure and description of how to make and use the embodiments of the binding compounds, compositions, devices, methods and systems for the selective detection, and are not intended to limit the scope of what the Applicants regard as their disclosure. Modifications of the above-described modes for carrying out the disclosure can be used by persons of skill in the art, and are intended to be within the scope of the following claims.

The entire disclosure of each document cited (including patents, patent applications, journal articles including related supplemental and/or supporting information sections, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure.

Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance can or cannot occur, so that the description includes instances where the circumstance occurs and instances where it does not according to the guidance provided in the present disclosure. Combinations envisioned can be identified in view of the desired features of the device in view of the present disclosure, and in view of the features that result in the formation.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claim.

The invention claimed is:

1. A system comprising
a porous membrane support structure having a lateral dimension in direction of a lateral flow and a second dimension perpendicular to the lateral dimension,
at least one primary support portion containing first binding compounds covalently bound to visual colloidal markers, capable of binding respective targets by forming first binding compound-target complexes with the respective targets, secondary support portions spaced and staggered in the lateral dimension each comprising second binding compounds covalently bound to the porous membrane support structure, the second binding compounds configured to bind either the targets or the first binding compound-target complexes, each second binding compound of the second binding compounds specific to a different target or different first binding compound-target complex of the respective targets, the second binding compounds being different from and non-competitive with the first binding compounds for said target, control regions spaced and staggered in the lateral dimension separate from and not overlapping with the secondary support portions and in a one-to-one correspondence with the secondary support portions such that every secondary support portion is adjacent to a corresponding control region, the control regions comprising third binding compounds configured to bind a respective first binding compound of the first binding compounds when unbound to the respective target, each control region configured to provide a control for the different targets at the secondary support portions, wherein lateral placement of each control region has a same lateral placement as its corresponding secondary support, a pH litmus indicator and a pH control strip that is separate from and not overlapping the pH litmus indicator, wherein the pH litmus indicator and the pH control strip are both located on the porous membrane support structure in the lateral dimension downstream of the secondary support portions, wherein lateral placement of the pH control strip is such that a lateral downstream end of the pH control strip has the same lateral position as the lateral downstream end of the pH litmus indicator, and a liquid medium for lateral flow on the support structure, configured to allow preservation and activity of binding compounds.

2. The system of claim 1, wherein the porous membrane support structure comprises a material selected from cellulose and nylon.

3. The system of claim 2, wherein the porous membrane support structure is portable and is configured for being hand held.

4. The system of claim 3, wherein the visual colloidal markers comprise materials selected from a colloidal material, a colloidal gold, a colloidal magnetic particle, and colloidal quantum dots.

5. The system of claim 1, wherein the second binding compounds are antibodies.

6. The system of claim 1, wherein the second binding compounds are not aptamers.

7. The system of claim 1, wherein the secondary support portions are periodically spaced with respect to each other.

8. The system of claim 1, wherein the first binding compounds are covalently bound to the visual colloidal markers through functional groups on the first binding compounds that interact with corresponding functional groups on the colloidal markers.

9. The system of claim 1, wherein the second binding compounds are each configured to specifically bind complex of a target of the respective targets and a first binding compound of the first binding compounds for said target.

10. The system of claim 1, wherein each control region has a shape indicative of a target of the respective targets.

11. The system of claim 1, wherein the porous membrane support structure is a textile strip.

* * * * *